United States Patent

Matoba et al.

Patent Number: 5,456,920
Date of Patent: Oct. 10, 1995

[54] UNCOATED TABLETS AND METHOD OF PRODUCING THE SAME

[75] Inventors: Hiroshi Matoba, Osaka; Hiroyoshi Koyama, Mishima; Jun-ichi Kikuta, Suita, all of Japan

[73] Assignee: Takeda Chemical Industries, Ltd., Osaka, Japan

[21] Appl. No.: 187,908

[22] Filed: Jan. 28, 1994

[30] Foreign Application Priority Data

Feb. 10, 1993 [JP] Japan ................... 5-045958

[51] Int. Cl.$^6$ .................................... A61K 9/20
[52] U.S. Cl. .................... 424/465; 424/464; 424/489; 424/490
[58] Field of Search .................... 424/464, 465, 424/490, 489

[56] References Cited

U.S. PATENT DOCUMENTS 5,055,304  10/1991  Makino et al. ............ 424/465

FOREIGN PATENT DOCUMENTS 0070127  1/1983  European Pat. Off. .
0546358  6/1993  European Pat. Off. .
4-25926  5/1992  Japan .

Primary Examiner—Thurman K. Page
Assistant Examiner—James M. Spear
Attorney, Agent, or Firm—Foley & Lardner

[57] ABSTRACT

A compression-moldable composition comprising an active ingredient, an excipient and an oily or fatty substance having a lower melting point of about 20° to 90° C. is compression-molded into uncoated tablets without coating to improve the abrasion resistance. The oily or fatty substance includes a higher fatty acid or a salt thereof, a wax, a fatty acid ester, a hardened oil, a polyalkylene oxide, etc., and the amount thereof is about 0.01 to 10% by weight. The composition may comprise (1) a granulated powder containing the active ingredient and the excipient, and the powdery or granular oily or fatty substance having a lower melting point, or (2) a granulated powder containing the active ingredient, the excipient and said oily or fatty substance. Compression-molding of the composition improves the abrasion resistance of the tablet and significantly inhibits the development of powder by wearing or abrasion even when the oily or fatty substance is used in a small amount of about 0.1 to 0.5% by weight.

26 Claims, No Drawings 5,456,920

UNCOATED TABLETS AND METHOD OF PRODUCING THE SAME

FIELD OF THE INVENTION

The present invention relates to an uncoated tablet having an improved abrasion resistance and usable in a variety of fields such as foods and drugs, and a method of producing such a tablet.

BACKGROUND OF THE INVENTION

Tablets can be classified into two major categories, i.e. (i) an uncoated tablet prepared by compression-molding fine granules, granules or a mixed powder and (ii) a coated tablet prepared by coating an uncoated tablet with a film or sugar. When the uncoated tablet has a curved surface, it may have problems with moldability. Thus, the uncoated tablet is usually molded into a flat form in order to insure productivity and handling efficiency.

Since the coated tablet has a smooth and mechanically strong surface, no powder is broken out due to wear or abrasion. Therefore, the coated tablet has advantages that it can be employed in a visual examination machine with a high handling and packaging efficiency, as well as in an automatic compounding machine in a hospital or pharmacy with an excellent handling efficiency. The coating layer of the coated tablet, however, suppresses disintegration of the tablet and dissolution of an active ingredient, thus it is unsuitable for a pharmaceutical preparation wherein fast disintegration or dissolution is required. Further, the coated tablet has disadvantages of being high costed owing to a large number of production steps.

On the contrary, though the above-mentioned uncoated tablet can be advantageously produced with ease and simplicity and with a low production cost, the surface thereof is worn or abraded in preparation or transportation process, and powder thus produced is attached or affixed to the surface of the uncoated tablet or remained in a package. Thus, the commercial value of the products is significantly reduced. Further, because of the powder attached or affixed to the tablet, the working efficiency in a visual examination machine and packaging efficiency may be reduced. Furthermore, the uncoated tablet also confronts with a lower working efficiency in an automatic compounding machine.

Regarding the techniques to suppress such development of powder due to wearing and abrading of an uncoated tablet, Japanese Patent Publication No. (JP-B) 25926/1992 discloses a coating method which comprises preparing a suspension or dispersion containing a higher fatty acid ester having a high melting point of 70° C. or more, a cellulose derivative soluble in a hydrophilic solvent and the hydrophilic solvent and coating the surface of an uncoated tablet with said suspension or dispersion in a proportion of 0.02 to 0.8% by weight on the dried basis.

This technique, however, requires a number of steps, that is, a step for preparing beforehand uncoated tablets by compression-molding, a step for preparing said suspension or dispersion by emulsifying or dispersing said higher fatty acid ester in a hydrophilic solvent using, if necessary, a surfactant, and a coating step for coating the tablets with said suspension or dispersion. Further, since the technique is a kind of coating techniques for coating the surface of tablets, the producing steps are complicated and an additional equipment for coating is further required to be arranged in the producing line of tablets.

It should be generally understood, as described in the above-mentioned literature, that even when a composition containing a lubricant is compressed and molded into a tablet, uncoated tablets having a practically satisfied abrasion resistance can not be obtained.

European Patent Application No. EP-546358 A2 discloses a stabilized pharmaceutical composition for oral use which is obtained by compression-molding a composition comprising the benzimidazole compound and an oily substance having a lower melting point, in order to suppressing decomposition of a benzimidazole compound as an active ingredient due to deformation of crystals caused by, for example, pressure.

U.S. Pat. No. 5,055,304 corresponding to Japanese Patent Application Laid-open No. (JP-A) 308231/1989 discloses a stabilized pharmaceutical composition which is obtained by compressing and molding a composition comprising disodium adenosine triphosphate and an oily substance having a lower melting point in order to suppressing the decomposition of disodium adenosine triphosphate.

In these literatures, said oily substances having lower melting points are used for stabilizing the active ingredients, and improvements in an abrasion resistance of an uncoated tablet were never taught by means of adding an oily substance having a lower melting point.

SUMMARY OF THE INVENTION

Accordingly, it is an object of the present invention to provide an uncoated tablet having an improved abrasion resistance without a coating layer of a coating composition and a method of producing the same.

It is another object of the invention to provide an uncoated tablet having a high abrasion resistance and capable of suppressing development of powder due to abrasion or wearing in spite of an exceedingly small amount of an additive and a method of producing such a tablet.

A still another object of the present invention is to provide an uncoated tablet which maintains readily disintegrating and/or dissolving properties with high abrasion resistance imparted and a method of producing the same.

It is a further object of the invention to provide a method for producing efficiently an uncoated tablet having an improved abrasion resistance with an easy and simple operation and requiring no complicated steps.

A still further object of the present invention is to provide a method of improving the abrasion resistance of an uncoated tablet by imparting an improved or enhanced abrasion resistance to said uncoated tablet.

After a great research effort to obtain an uncoated tablet having the advantages both of an uncoated tablet and a coated tablet as mentioned above, the inventors of the present invention found that when a compression-moldable composition containing an oily or fatty substance of a lower melting point is compressed and molded into a tablet without coating, the resulting uncoated tablet has a significantly improved abrasion resistance even when a small amount of said oily or fatty substance is employed. Thus, the present invention was accomplished based on the above findings.

Accordingly, an uncoated tablet having an improved abrasion resistance of the present invention comprises an active ingredient, an excipient and an oily or fatty substance having a lower melting point. Said oily or fatty substance includes, for example, a hydrophilic or water-soluble substance and a fat-soluble or water-insoluble substance. The melting point of said oily or fatty substance may be, for example, about 20° to 90° C. The content of said oily or fatty substance is selected from, for example, about 0.01 to 10% by weight based on the total weight of the uncoated tablet depending on the objects, and even when the proportion of said substance is as small as 0.1% by weight or more and less than 0.5% by weight, the abrasion resistance of the uncoated tablet can be remarkably improved.

According to the method of the invention, an uncoated tablet improved in an abrasion resistance can be produced by incorporating an oily or fatty substance having a lower melting point into a compression-moldable composition. Said method includes, for instance, (1) a method which comprises compressing and molding the compression-moldable composition comprising a granulated powder containing an active ingredient and an excipient, and said oily or fatty substance having a lower melting point, and (2) a method which comprises compressing and molding the compression-moldable composition comprising a granulated powder containing an active ingredient, an excipient and the oily or fatty substance. In the method (1), the oily or fatty substance in powdery or granular form may be used. Said granulated powder may be obtained by, for example, a wet-granulation.

Further, the present invention also provides a method of improving an abrasion resistance of an uncoated tablet by way of incorporating an oily or fatty substance having a lower melting point into an active ingredient. Said method may comprise compression-molding a moldable composition comprising 0.1% by weight or more and less than 0.5% by weight of said oily or fatty substance based on the total weight of the uncoated tablet to improve the abrasion resistance of the tablet.

DETAILED DESCRIPTION OF THE INVENTION

As used through out in this specification, the term "granulated powder" means to also include comminuted powder obtainable by comminuting or milling granulated preparations such as fine granules and granules in a conventional manner such as comminuting and classifying. In cases where the oily or fatty substance is not a single compound but a mixture, the substance does not show a distinct melting point but softens at a specific temperature. The term "melting point" as used in this specification includes, within the meaning thereof, the softening point of such a mixture as well.

The oily or fatty substance having a lower melting point can be selected from a variety of substances with a high safety, for example, compounds generally approved as pharmaceutical additives. Among them, preferable examples of the oily or fatty substance include an oily or fatty substance having a lower melting point and being liable to be plastically deformed or expandable under a molding pressure. The specifically preferred oily or fatty substance includes a substance capable of being pulverized to fine powder.

The melting point of said oily or fatty substance is, for example, usually about 20° to 90° C., and preferably about 20° to 80° C., and more preferably about 20° to 60° C. The melting point of the oily or fatty substance is frequently about 40° to 75° C. When the melting point of said substance is less than 20° C., the strength of the uncoated tablet is occasionally reduced depending on an amount of said substance to be added, and, contrarily, when the melting point of said substance exceeds 90° C., the abrasion resistance of the uncoated tablet may not be so remarkably increased in case of molding under a conventional compression-molding pressure.

The oily or fatty substance having a lower melting point may be a hydrophilic or water-soluble substance such as a polymer of an alkylene oxide and a derivative of a poly(alkylene oxide) as mentioned hereinafter, or a fat-soluble or water-insoluble substance such as a hydrocarbon, a wax and a fatty acid ester.

As examples of the oily or fatty substance having a lower melting point, there may be mentioned a hydrocarbon, a higher fatty acid or a salt thereof, a higher alcohol, a wax, a hardened oil, a fatty acid ester, a higher alcohol ether of a polyhydric alcohol, a homopolymer or copolymer of an alkylene oxide and the like.

The hydrocarbon includes an aliphatic hydrocarbon of about 17 to 60 carbon atoms, for example, straight or branched hydrocarbons such as n-heptadecane, n-octadecane, n-nonadecane, n-icosane, n-henicosane, n-docosane, n-tricosane, n-tetracosane, n-pentacosane, n-triacontane, n-tetracontane, n-pentacontane and n-hexacontane; a mixture of these hydrocarbons.

The higher fatty acid may be a saturated fatty acid or an unsaturated fatty acid. As examples of the higher fatty acid, there may be mentioned a saturated fatty acid such as caprylic acid, lauric acid, myristic acid, palmitic acid, stearic acid, arachic acid, behenic acid, lignoceric acid, cerotic acid and montaic acid; an unsaturated fatty acid such as elaidic acid, isooleic acid and erucic acid; a higher fatty acid obtainable from a naturally-occurring fat and oil; and a mixture of said fatty acids. The higher fatty acid may have, for example, about 10 to 40 carbon atoms and preferably about 10 to 30 carbon atoms, and a saturated higher fatty acid of about 12 to 22 carbon atoms is practically preferred among them.

The higher fatty acid can also be used as a salt, for example, a salt with an alkali metal such as sodium and potassium, a salt with an alkaline earth metal such as calcium, and others.

The higher alcohol includes a saturated alcohol and an unsaturated alcohol. Examples of species of the higher alcohol include lauryl alcohol, tetradecyl alcohol, myristyl alcohol, cetyl alcohol, stearyl alcohol, arachyl alcohol, higher alcohols collectable from naturally-occurring fats and oils and a mixture of these alcohols. The higher alcohol may contain, for example, about 10 to 35 of carbon atoms. Among them, a saturated higher alcohol of about 16 to 22 carbon atoms may be practically employed.

Examples of the wax include paraffin wax, carnauba wax, candelilla wax, beeswax, montan wax, spermaceti wax, shellac wax, microcrystalline wax, petrolatum and so on.

As examples of the hardened oil, there may be mentioned a hardened vegetable oil such as castor oil, rapeseed oil, cottonseed oil, soybean oil, coconut oil, palm kernel oil and palm oil; a hardened animal oil such as beef oil and whale oil; and the like.

The fatty acid ester may be an ester of monohydric higher alcohol with a fatty acid (wax ester) such as cetyl palmitate, ceryl palmitate, myricyl palmitate, ceryl cerotate and melissyl melissate. As the fatty acid ester, an ester of a polyhydric alcohol having two or more hydroxyl groups in the molecule with a fatty acid is frequently used. Examples of said polyhydric alcohol include alkylene glycols such as ethylene glycol and propylene glycol; poly(alkylene glycol) such as diethylene glycol, triethylene glycol, poly(ethylene glycol), dipropylene glycol, tripropylene glycol, poly(propylene glycol) and copolymers of these glycols; polyhydric alcohols such as glycerin, polyglycerin and pentaerythritol; sugars such as sorbitol, sucrose and raffinose; intramolecular dehydrates derived from sorbitol such as 1,5-sorbitan, 1,4-sorbitol and 3,6-sorbitan; di- or trialkanolamines such as diethanolamine and triethanolamine. Said fatty acid is exemplified as saturated fatty acid such as acetic acid, propionic acid, butyric acid, pelargonic acid, lauric acid, myristic acid, palmitic acid, heptadecylic acid, stearic acid, behenic acid, nonadecanoic acid and undecylic acid; and unsaturated fatty acid such as oleic acid, sorbic acid, linoleic acid, linolenic acid, arachidonic acid and stearolic acid.

Typical examples of the fatty acid ester of polyhydric alcohol include sorbitan fatty acid esters having a molecular weight of about 400 to 900 (for example, sorbitan monostearate, sorbitan tristearate, sorbitan monooleate, sorbitan sesquistearate, sorbitan monopalmitate, etc.); polyoxyalkylene sorbitan fatty acid esters having a molecular weight of about 1,000 to 1,500 (e.g. polyoxyethylene sorbitan tripalmitate, etc.); polyoxyalkylene sorbitol fatty acid esters such as polyoxyethylene sorbitol hexastearate, polyoxyethylene sorbitol hexaoleate, polyoxyethylene sorbitol tristearate, polyoxyethylene sorbitol tetralaurate and others; polyoxyalkylene sorbitol beeswax derivatives such as polyoxyethylene sorbitol beeswax derivatives, etc.; polyoxyalkylene hydrous lanolin derivatives such as polyoxyethylene lanolin derivatives, etc.; alkylene glycol fatty acid esters including propylene glycol fatty acid esters having molecular weights of about 200 to 700 (for example, propylene glycol monopalmitate, propylene glycol monostearate, propylene glycol dilaurate, propylene glycol dimyristate, propylene glycol dipalmitate, propylene glycol distearate, etc.) and ethylene glycol fatty acid esters having molecular weights of about 500 to 1,200 (e.g. ethylene glycol monolaurate, ethylene glycol monopalmitate, ethylene glycol monomargarate, ethylene glycol monostearate, ethylene glycol dilaurate, ethylene glycol dimyristate, ethylene glycol dipalmitate, ethylene glycol dimargarate and the like); polyoxyalkylene castor oil derivatives having molecular weights of about 3,500 to 4,000 (for example, polyoxyethylene castor oil derivatives, etc.); polyoxyalkylene fatty acid esters having molecular weights of about 1,900 to 2,200 (e.g. polyoxyethylene stearate, polyoxyethylene oleate, polyoxyethylene palmitate, polyoxyethylene linoleate, and so on); glycerol fatty acid esters having molecular weights of about 300 to 600 (for instance, glycerol monofatty acid esters such as glycerol monoacetate, glycerol monopropionate, glycerol monocaprylate, glycerol monolaurate, glycerol monomyristate, glycerol monopalmitate, glycerol monostearate, glycerol monooleate and glycerol monolinoleate; glycerol difatty acid esters such as glycerol dicaprylate, glycerol dilaurate, glycerol dimyristate, glycerol dipalmitate and glycerol distearate; and glycerol trifatty acid esters such as glycerol tricaprylate, glycerol trilaurate, glycerol trimyristate, glycerol tripalmitate and glycerol tristearate); polyglycerol fatty acid esters; sucrose fatty acid esters having a molecular weight of about 400 to 1,300 (e.g. sucrose monolaurate, sucrose monomyristate, sucrose monopalmitate, sucrose monostearate, sucrose distearate, sucrose trimyristate, sucrose tripalmitate, sucrose tristearate, etc.); and the like.

The higher alcohol ether of polyhydric alcohol includes, for example, ethers formed by etherification of a polyhydric alcohol (set forth as alcohol components of the fatty acid ester of polyhydric alcohol mentioned above) with a higher alcohol (for instance, the higher alcohols mentioned above, as well as oleyl alcohol, octyl alcohol, decyl alcohol and the like).

Typical examples of the ether mentioned above include polyoxyethylene higher alcohol ethers (e.g. polyoxyethylene lauryl alcohol ether, polyoxyethylene cetyl alcohol ether, polyoxyethylene stearyl alcohol ether, polyoxyethylene oleyl alcohol ether, polyoxyethylene octyl alcohol ether, polyoxyethylene decyl alcohol ether, etc.); polyoxypropylene polyoxyethylene higher alcohol ethers (e.g. polyoxypropylene polyoxyethylene cetyl alcohol ether, polyoxypropylene polyoxyethylene stearyl alcohol ether, polyoxypropylene polyoxyethylene oleyl alcohol ether, polyoxypropylene polyoxyethylene octyl alcohol ether, polyoxypropylene polyoxyethylene lauryl alcohol ether, etc.).

The polymer of alkylene oxide may be homopolymers of alkylene oxides such as ethylene oxide, propylene oxide, trimethylene oxide and tetrahydrofuran, or copolymers of alkylene oxides. Preferred alkylene oxide includes ethylene oxide.

As the homopolymer of alkylene oxide, use is made of those having a molecular weight of about 1,000 to 50,000 and preferably about 1,500 to 30,000 (e.g. polyethylene glycol 6,000) and so on.

The copolymer of an alkylene oxide includes, for example, a copolymer of two or more species of the above-mentioned alkylene oxides, which has a molecular weight of about 1,000 to 50,000. Said copolymer of alkylene oxide may be a random copolymer or a block copolymer. As the copolymer, a copolymer containing an oxyethylene unit obtainable by copolymerizing ethylene oxide and other alkylene oxide, practically a copolymer formed with ethylene oxide and propylene oxide can be employed. Examples of said copolymer include a poly(ethylene oxide-propylene oxide) copolymer [for example, PEP-101 (trade name, Freund Industrial Co., Ltd.; Japan) and Pullronic F68 (trade name, Asahi Denka Co., Ltd.; Japan)] and the like. The content of the oxyethylene unit in the copolymer is, for example, about 50 to 95% by weight, preferably about 60 to 90% by weight.

Preferred examples of the alkylene oxide polymer include a homo- or copolymer of ethylene oxide, especially polyethylene glycol.

These oily or fatty substances having lower melting points can be used singly or in combination. When two or more species of oily or fatty substances having lower melting points are used as a mixture, one or more of the oily or fatty substances can have melting points of less than 20° C. or more than 90° C., as far as said mixture remains solid in the prescribed melting point of 20° to 90° C.

The practically preferable oily or fatty substance having a lower melting point includes a higher fatty acid, a wax, a fatty acid ester, a higher alcohol ether of a polyhydric alcohol, a homopolymer or copolymer of an alkylene oxide. Among these substances, a homopolymer or copolymers of an alkylene oxide may advantageously employed.

When a fat-soluble or water-insoluble oily or fatty substance is used, the sustained releasability of the active ingredient can be liable to exhibit. On the contrary, use of a hydrophilic or water-soluble oily or fatty substance remarkably improves, even when the amount of said substance is small, the abrasion resistance of the uncoated tablet with high disintegration and solubility, thus the effects of the active ingredient can be exhibited readily. Therefore, when demanded is an uncoated tablet which has high disintegrating properties and solubility maintained and is capable of acting readily, the uncoated tablet may preferably comprise a hydrophilic oily or fatty substance, especially water-soluble oily or fatty substance.

The hydrophilic or the water-soluble oily or fatty substance include, for example, a higher alcohol ether of a polyhydric alcohol, an alkylene oxide derivative formed by reacting a fatty acid ester having one or more of hydroxyl groups with an alkylene oxide (particularly, ethylene oxide), a homo- or copolymer of an alkylene oxide and others. Preferred examples of the oily or fatty substance include an oily or fatty substance having an oxyalkylene unit such as oxyethylene unit. More specifically, a water-soluble oily or fatty substance such as a polyhydric alcohol, especially a homo- or copolymer of an alkylene oxide having oxyethylene unit is preferred. As the water-soluble oily or fatty substance, polyethylene glycol may advantageously be employed.

The content of the oily or fatty substance having a lower melting point in the uncoated tablet is depending on a kind of the active ingredient or properties of the additive, and is for example, from about 0.01 to 10% by weight, preferably from about 0.1 to 5% by weight, and more preferably from about 0.1 to 3% by weight based on the total weight of the tablet. The abrasion resistance of the uncoated tablet would not be so much improved when the content of the oily or fatty substance is less than 0.01% by weight, and, contrarily, the physical or chemical properties of the uncoated tablet and dissolution properties of the active ingredient may be adversely affected when the content of the oily or fatty substance exceeds 10% by weight.

As mentioned above, in order to improve the sustained releasability, tablets containing a large amount of a lipid such as a fatty acid ester have been well known. Still, the uncoated tablet of the present invention is characterized in that it exhibits an excellent abrasion resistance by means of adding a small or slight amount of the oily or fatty substance having a lower melting point. Accordingly, an uncoated tablet can be improved in the abrasion resistance with development of powder being significantly suppressed even when the content of the oily or fatty substance having a lower melting point based on the total weight of the tablet is extremely small, for example, 0.1% by weight or more and less than 0.5% by weight (preferably about 0.1 to 0.45% by weight, and more preferably about 0.2 to 0.4% by weight). Further, when a small amount of an hydrophilic or water-soluble oily or fatty substance is incorporated into the tablet, the disintegration of the uncoated tablet and dissolution of the active ingredient are not suppressed.

The present invention can be applied to uncoated tablets in a variety of fields, including drugs for human beings such as medicines (drugs) and quasi drugs; animal drugs; agrochemicals containing, for example, a bactericide, an insecticide, a herbicide, a raticide, a repellent, a plant growth regulator, etc. as an active ingredient; a diet containing an amino acid, a peptide, a nucleic acid, an organic acid or others as an active ingredient; and so on. Thus the active ingredient used in the present invention is not critically restricted.

Examples of the drug include central nervous drugs such as antipyretic, analgesic and/or antiinflammatory agents, hypnotics and sedatives, psychotropics and neuropharmaceuticals, agent for peripheral nervous; peripheral nervous drugs such as skeletal muscle relaxants and autonomic drugs; circulatory drugs such as cardiotonics, antiarrhythmic agents, diuretics and vasodilators; respiratory organ drugs such as bronchodilators and antitussives; digestive organ drugs such as digestants, intestinal function controlling agents and antacids; hormones; antihistaminics; metabolic drugs such as vitamins; antiulcer drugs; antibiotics; chemotherapeutic agents; and so on.

Among such drugs for doctors and pharmacy, a drug having a comparatively high stability for environmental factors such as light or requiring no corrigent and others is frequently administered as an uncoated tablet. The present invention can be applied suitably to such drugs.

Examples of active ingredients in such drugs and the like include delapril hydrochloride, ipriflavone, manidipine hydrochloride, dexamethasone, alprazolam, diazepam, amlexanox, sodium liothyronine, perlapine, prednisolone, griseofulvin, estazolam, vinpocetine, labetalol hydrochloride, idebenone, fursultiamine, chlordiazepoxide, pyridoxal phosphate, ranitidine hydrochloride, nifedipine, lovastatin, cefaclor, cimetidine, fluoxetine hydrochloride, enalapril maleate, naproxen, captopril, terfenadine, atenolol, verapamil hydrochloride, ciprofloxacin hydrochloride, diclofenac sodium, piroxicam, pravastatin sodium, famotidine, nicardipine hydrochloride, ticlopidine hydrochloride, teprenone, ofloxacin, ketotifen fumarate, oxatomide, azulene, mecobalamin, cefixime, indeloxazine hydrochloride, nicergorine, loxoprofen sodium, alfacalcidol, diltiazem hydrochloride, bifemelane hydrochloride, azelastine hydrochloride, domperidone, fluconazole, norfloxacin, (±)-7-(3,5, 6,-trimethyl-1,4-benzoquinon-2-yl)-7-phenylheptanoic acid, (E)-7-phenyl-7-(3-pyridyl)-6-heptenoic acid, 2-(7-chloro-1, 8-naphthyridin-2-yl)-3-(1,4-dioxa-8-azaspiro[4.5]dec-8-yl) carbonylmethylisoindolin-1-one (hereinafter abbreviated as Compound A), (+)-1L-[1(OH),2,4,5/3]-5-[2-hydroxy-1(hydroxymethyl)ethyl]amino-1-C-(hydroxymethyl)-1,2,3,4-cyclohexanetrol or N-(1,3-dihydroxy-2-propyl)valiolamine (voglibose, hereinafter abbreviated as Compound B), (±)-3, 4-dihydro-2,8-diisopropyl-3-thioxo-2H-1,4-benzoxazine-4-acetic acid, 5-[4-[2-(5-ethyl-2pyridyl)ethoxy]benzyl]-2,4-thiazolidindione hydrochloride, 3-[1-(phenylmethyl)piperidin-4-yl]-1-(2,3,4,5-tetrahydro-1H-1-benzazepin-8-yl)-1-propanone fumarate, 2-(6-bromo-7-chloro-2,2-dimethyl-2H-1,3-benzoxazine-4-yl)pyridine 1-oxide, 2-[[[3-methyl-4-(2,2,3,3-tetrafluoropropoxy)-2-pyridyl]methyl]thio]benzimidazole, N-[4-(2-chlorophenyl)-7,8-dihydro-6H-cyclopenta[g]quinolin-3-yl]-N'-(2,4-dichlorophenyl)urea, sodium 1-hydroxy-2-(3-pyridinyl)ethylidynebisphosphonate, 2-ethyl-2-[(7-methyl-[1,2,4]triazolo[1,5-b]pyridazin-6-yl)-oxymethyl]butanesulfonamide, indomethacin, salicylic acid, trepibutone, amoxanox, aspirin, valproic acid, ketoprofen, ibuprofen, probenecid, isosorbide dinitrate, quinidine, morphine, dihydrocodeine phosphate, ephedrine, scopolamine, chlorpromazine, phenylpropanolamine hydrochloride, chlorpheniramine maleate, sulfanilamide, molsidomine, sulfadiazine, acetaminophen, theophyline, caffeine, cephalexin, ampicillin, sulfisoxazole, cefotiam hexetil hydrochloride, cyclandelate, propranolol, haloperidol, chlorothiazide, hydrochlorothiazide, sucralfate, vitamins such as riboflavin, ascorbic acid, etc., minerals, amino acids, peptides or proteins (for example, insulin, vasopressin, interferon, IL-2, urokinase, serratiopeptidase, somatostatin, growth hormone and growth factors), and the like.

The proportion of the active ingredient to be contained in the uncoated tablet of the present invention can be suitably selected from a wide level depending on species of the active ingredient or others, and is, for example, about 0.001 to 90% by weight, preferably about 0.01 to 50% by weight, and more preferably about 0.1 to 25% by weight based on the total weight of the tablet.

The uncoated tablet of the present invention usually contains an excipient in addition to the oily or fatty substance having a lower melting point and the active ingredient. As examples of the excipient, there may be mentioned lactose, starch, corn starch, crystalline cellulose [e.g. Avicel PH101 (trade name, Asahi Kasei Co., Ltd.), etc.], powder sugar, granulated sugar, mannitol, light silicic anhydride, magnesium carbonate, calcium carbonate, L-cysteine and so on. These excipients can be used independently or in combination. The content of the excipient may range, for example, from about 25 to 99.5% by weight, preferably from about 40 to 99% by weight, and more preferably from about 50 to 96% by weight.

The uncoated tablet of the present invention may further comprise conventional additives usable in solid pharmaceutical preparations. Such additives include, for example, binders (e.g. sucrose, gelatin, gum arabic, methylcellulose, hydroxypropylcellulose, hydroxypropylmethylcellulose, carboxymethylcellulose, carboxymethylcellulose sodium, polyvinylpyrrolidone, pullulan, dextrin, etc.); disintegrators (e.g. carboxymethylcellulose calcium, croscarmellose sodium [for example, Acdisol (trade name, Asahi Kasei Co., Ltd.)], crosslinked insoluble polyvinylpyrrolidone [e.g. Colidone CL (trade name, BASF Ltd.)], low-substituted hydroxypropylcellulose, partial alpha-starch, etc.); enteric polymers (for instance, hyrdroxypropylmethylcellulose phthalate, cellulose acetate phthalate, carboxymethylethylcellulose and so on); water-insoluble polymers (e.g. aminoalkylmethacrylate copolymers, methacrylic acid copolymers, etc.); lubricants (for example, magnesium stearate, talc and the like); surfactants (e.g. anionic surfactants such as sodium alkylsulfates, etc., and nonionic surfactants such as polyoxyethylene sorbitan fatty acid esters, polyoxyethylene fatty acid esters, polyoxyethylene castor oil derivatives, etc.); colorants (for instance, tar pigments, caramel, iron red oxide, titanium oxide, riboflavin, etc.); corrigents (e.g. sweeteners, flavors and the like); adsorbents; preservatives; wetting agents; antistatic agents; disintegration retarders; and others.

The uncoated tablet of the present invention may frequently be comprised of the binder. The amount of the binder to be used is, for example, about 0.5 to 30% by weight, and preferably about 1 to 10% by weight based on the total weight of the tablet.

In the uncoated tablet of the invention, the oily or fatty substance having a lower melting point is presumably dispersed in the uncoated tablet and is expanded (extended) and developed at least on the surface of the tablet. In such an uncoated tablet, the oily or fatty substance having a lower melting point may be dispersed independently or in combination with other ingredients such as the active ingredient and excipient. The oily or fatty substance can also be expanded and/or developed not only on the surface but also over the whole of the tablet including the neighborhood of the surface of the tablet.

Further, the oily or fatty substance having a lower melting point may be typically dispersed in the tablet in the powdery or granular form. In such a tablet, it is presumed that the powdery or granular oily or fatty substance at least on the surface of the tablet would be expanded or extended by means of the compression-molding pressure (compacting pressure).

The uncoated tablet of the present invention has an outstanding feature of having a high abrasion resistance without coating of a coating composition. That is, according to the invention, the frictional force of the tablet by an external force is reduced by the oily or fatty substance, and the abrasion resistance of the tablet can be enhanced. Thus wear or attrition of said tablet is significantly reduced and the development of powder can be suppressed. Further, the strength of the tablet is not diminished, probably because the plastically-deformed oily or fatty substance having a lower melting point by compression-mold fixes surrounding particles. Therefore, when the tablet is orally administered, the disintegration of the tablet and the dissolution of the active ingredient are not sustained, thus readily-acting tablets can also be obtained. Furthermore, the tablet has a high working efficiency in operation of an automatic compounding machine in a hospital or pharmacy without development of powder in a distribution stage, accordingly the commercial value of the tablet can be enhanced.

As apparent from the abrasion resistance test of the examples mentioned below, the uncoated tablet of the invention shows a reflectance of about 0.01 to 0.3, preferably about 0.01 to 0.2, and more preferably about 0.03 to 0.1, on condition that 50 g of the uncoated tablets in a white bottle (inner volume of 80 ml) is shaken for 30 minutes at a shaking rate of 220 times per minute and amplitude of 40 mm, and the reflectance at a wave length of 500 nm is determined as an extent or degree of hazing (cloudiness) at the bottom of the bottle. On the contrary, the reflectance of an uncoated tablet containing no oily or fatty substance having a lower melting point is 0.4 or more.

The uncoated tablet improved in the abrasion resistance of the present invention can be produced by incorporating the oily or fatty substance into the active ingredient, specifically into a compression-moldable composition containing said active ingredient, by means of, for example, blending, mixing or granulating, followed by subjecting the mixture to molding. The uncoated tablet can usually be produced by compression-molding a moldable composition comprising the above-mentioned active ingredient, excipient, oily or fatty substance having a lower melting point, and, if necessary, additives as above. Thus, an improved and/or enhanced abrasion resistance of the uncoated tablet can be realized by incorporating the oily or fatty substance having a lower melting point into the active ingredient by an incorporating means such as blending, mixing, combining, adding or granulating.

The uncoated tablet can also be produced by subjecting said compression-moldable composition comprising the oily or fatty substance having a lower melting point directly to pressure-molding (compression-molding). In such a manner, the oily or fatty substance having a lower melting point may be added as liquid or solid. The oily or fatty substance having a lower melting point may usually be added as powdery or granular form, for example, with a mean particle size of about 1,000 µm or less, preferably about 0.1 to 750 µm, and more preferably about 1 to 500 µm. When powdery or granular oily or fatty substance having a lower melting point is employed, such an excellent uncoated tablet as mentioned above can be obtained by such a simple and easy manner of blending or mixing and compression-molding.

According to the method of the invention, a compression-moldable composition comprising a granulated powder containing the active ingredient and the excipient, and the oily or fatty substance having a lower melting point (preferably powdery or granular oily or fatty substance having a lower melting point) can also be compressed and molded into uncoated tablets. Said method is characterized in that the oily or fatty substance having a lower melting point is admixed to the granulated powder, and the mixture is compressed and molded into tablets, while the oily or fatty substance is not used for granulation. While lipids such as a fatty acid ester and a wax conventionally employed as a component of tablets are usually used in the granulation.

The granulated powder may be prepared by a conventional manner such as a wet-granulation and a dry-granulation, with use of a binder. The granulated powder may preferably be obtained by wet-granulating techniques such as a stirring-granulation and a fluidized-bed granulation wherein granulation can be conducted without the use of the oily or fatty substance having a lower melting point or, if used, with only a slight amount of said substance. The typical examples of the granulated powder usually include fine granules, granules and comminuted powder obtainable from granulated preparations. The mean particle size of the granulated powder is, for example, about 0.1 to 10,000 μm, preferably about 10 to 2,000 μm, and most preferably about 74 to 1,400 μm.

The composition including such granulated powder and the oily or fatty substance having a lower melting point can be prepared by a conventional manner such as blending or mixing, and thus obtained compression-moldable composition is compression-molded into uncoated tablets.

When the oily or fatty substance having a lower melting point is soluble or dispersible in water, a hydrophilic solvent (e.g. alcohols such as methanol and isopropanol, acetone and the like), or a hydrophobic solvent (e.g. hexane, ethers such as diethylether, esters such as ethyl acetate, etc.), said oily or fatty substance can be used as a solution or dispersion. The preferable examples of the solvent include a hydrophilic solvent, and water can advantageously be employed. The preferred oily or fatty substance includes a hydrophilic oily or fatty substance capable of dissolving or dispersing in the preferred solvent as above, especially a water-soluble oily or fatty substance.

When the solution or dispersion containing the oily or fatty substance having a low melting point is employed, the granulated powder comprising the active ingredient, the excipient and the oily or fatty substance having a lower melting point is obtainable by a wet-granulating means such as a stirring-granulation and a fluidized-bed granulation.

The compression-moldable composition may further comprise other additives such as disintegrators and lubricants in addition to the above-mentioned components.

The compacting pressure (compression-molding pressure) can be selected from the range where the abrasion resistance of the uncoated tablet is not adversely affected, and is usually about 100 to 5,000 kg/cm$^2$ and preferably about 500 to 3,000 kg/cm$^2$.

Typically preferred embodiments of the method of the present invention include (1) a process which comprises pressure-molding the moldable composition comprising the granulated powder containing the active ingredient, excipient and others, and the powdery or granular oily or fatty substance having a lower melting point, (2) a process which comprises pressure-molding the moldable composition containing the granulated powder comprising the active ingredient, the excipient and the oily or fatty substance having a lower melting point, and the like. In these processes, the moldable composition, especially the granulated powder, may frequently further comprise the binder.

Thus, the uncoated tablet of the present invention can significantly be improved in the abrasion resistance with less probability of development of powder, therefore, the working efficiency and/or packaging efficiency in a visual examination machine and automatic compounding machine can extremely be enhanced.

According to the present invention, a small amount of the oily or fatty substance having a lower melting point significantly enhance the abrasion resistance of the uncoated tablet without coating, therefore, even when a frictional or impact force acts on the tablet in production, transportation, compounding or the other processes, the development or occurrence of fine powder or powder dust due to wear or abrasion can efficaciously be inhibited. Further, the uncoated tablet is also superb in tablet characteristics such as strength, disintegrating properties and solubility. Furthermore, even when said oily or fatty substance is incorporated into the tablet in an exceedingly small amount, the uncoated tablet can be quite improved in the abrasion resistance and the development of powder or powder dust can efficiently be suppressed. When a water-soluble oily or fatty substance is employed as the oily or fatty substance, the disintegration properties and/or dissolving properties can also be advanced.

According to the method of the invention, the uncoated tablet having such excellent characteristics as above can efficiently be produced by a simple operation and easy manner of compression-molding, without coating of a coating composition and a complicated process. Further, an elevated abrasion resistance can be imparted to the uncoated tablet by incorporating a small amount of the oily or fatty substance having a lower melting point.

The following examples are intended to describe the present invention in further detail and should by no means be interpreted as defining the scope of the invention.

EXAMPLES

Examples 1 to 6

A fluidized-bed granulator (model:FD-3S, manufactured by Powrex Corporation, Japan) was charged with 32.0 g of 2-(7-chloro-1,8-naphthyridin-2-yl)-3-(1,4-dioxa- 8-azaspiro [4.5]dec-8-yl)carbonylmethylisoindolin- 1-one (Compound A), 756.8 g of lactose and 144.0 g of corn starch, and the charge was fluidized-bed granulated while 451.2 g of an aqueous solution of 6% by weight of hydroxypropylcellulose was sprayed at a feed air temperature of 70° C., under a pressure of 1.0 kg/cm$^2$ and at a rate of 10 g per minute, and the granulation products were dried and cooled to a temperature of 45° C. with fluidization or floating. The resulting granules were comminuted with a mill (Power Mill, with a screen of 1.2 mm φ, Showa Chemical Ltd., Japan) to prepare comminuted powder. Further, the preparation process as above was repeated to obtain 6 batches of comminuted powder.

Subsequently, using the comminuted powder thus obtained, mixed powders each containing different amount of polyethylene glycol 6,000 were prepared. That is, a mixture of 2.8 g of magnesium stearate, a predetermined amount of pulverized product of polyethylene glycol 6,000 [milled with an Atomizer (Fuji Paudal Co., Ltd.); screen size: 1 mm φ] and corn starch was sieved with a round sieve No. 30 (sieve opening of 500 μm), and the sieved was blended with 840.0 g of the comminuted powder in a Tumbler Mixer (model: TM-15, Showa Chemical Ltd., Japan) for 5 minutes to prepare 910 g of a mixed powder.

The amount of polyethylene glycol 6,000 to be added in each Example was, respectively, 0.9 g (Example 1, corresponding to 0.1% by weight based on the total weight), 1.8 g (Example 2, 0.2% by weight), 3.6 g (Example 3, 0.4% by weight), 5.5 g (Example 4, 0.6% by weight), 9.1 g (Example 5, 1.0% by weight) and 27.3 g (Example 6, 3.0% by weight) and corn starch was added to adjust the total weight to 910 g.

These mixed powders were compression-molded with a rotary tablet machine (Clean Press Correct 19K, Kikusui Seisakusho Co., Ltd., Japan) with a punch of 7 mm φ at a compacting pressure of 1,000 kg per punch and a thickness of the tablet of about 2.5 mm to prepare uncoated tablets (weight: 130.0 mg per tablet).

Said tablets contain, per tablet, 120.0 mg of the comminuted powder (comprising 4.0 mg of Compound A, 94.6 mg of lactose, 18.0 mg of corn starch and 3.4 mg of hydroxypropylcellulose), 0.4 mg of magnesium stearate, about 0.13 to 3.9 mg of polyethylene glycol 6,000 and about 9.5 to 5.7 mg of corn starch.

Comparative Example 1

An uncoated tablet was prepared in the same manner as in Example 1 except that the corn starch was used instead of polyethylene glycol 6,000. The tablets thus obtained contain 120.0 mg of the comminuted powder obtained in Example 1, 9.6 mg of corn starch and 0.4 mg of magnesium stearate, per tablet (130.0 mg).

Comparative Example 2

A comminuted powder was prepared in the same manner as in Example 1, except for using lactose instead of the active ingredient of Example 1. Namely, using 788.8 g of lactose, 144.0 g of corn starch and 451.2 g of an aqueous solution of 6% by weight of hydroxypropylmethylcellulose, the mixture was fluidized-bed granulated and dried, and the dried granules were comminuted to prepare comminuted powder in the same manner as in Example 1.

Corn starch (67.2 g) and magnesium stearate (2.8 g) were added to 840.0 g of the comminuted powder thus obtained, and 910 g of the resulting mixture was tabletted as in Example 1 to provide uncoated tablets.

The uncoated tablets contain, per tablet (130.0 mg), 120.0 mg of the comminuted powder (composed of 98.6 mg of lactose, 18.0 mg of corn starch and 3.4 mg of hydroxypropylcellulose), 9.6 mg of corn starch and 0.4 mg of magnesium stearate.

Example 7

The same fluidized-bed granulator as used in Example 1 was charged with 820.8 g of lactose and 160.0 g of corn starch, and the charge was fluidized-bed granulated while 510.4 g of an aqueous solution of 6% by weight of hydroxypropylcellulose containing 1.6 g of (+)-1L-[1(OH), 2,4,5/3]-5-[2-hydroxy-1-(hydroxymethyl) ethyl]amino-1-C-(hydroxymethyl)-1,2,3,4cyclohexanetrol, namely, N-(1,3-dihydroxy-2-propyl)valiolamine (voglibose, Compound B) was sprayed at a feed air temperature of 70.0° C., at a pressure of 1.0 kg/cm² and a rate of 10 g per minute, and the granulation product was dried and cooled to 45° C. with fluidization or floating. The resulting granules were comminuted with the same mill (Power Mill) used in Example 1 to prepare a comminuted powder.

To 886.2 g of the comminuted powder thus obtained were added 17.5 g of corn starch, 2.8 g of magnesium stearate and 3.5 g of polyethylene glycol 6,000 (about 0.38% by weight based on the total weight) milled with the Atomizer used in Example 1, and a mixed powder (910 g) was obtained in the same manner as in Example 1. The mixed powder was compression-molded in the same manner as Example 1 to provide uncoated tablets.

The uncoated tablets comprise, per tablet (130 mg), 126.6 mg of the comminuted powder (containing 0.2 mg of Compound B, 102.6 mg of lactose, 20.0 mg of corn starch and 3.8 mg of hydroxypropylcellulose), 2.5 mg of corn starch, 0.4 mg of magnesium stearate and 0.5 mg of polyethylene glycol 6,000.

Comparative Example 3

To the comminuted powder obtained in Example 7 were added 21.0 g of corn starch and 2.8 g of magnesium stearate, and a mixed powder (910 g) was prepared in the same procedure as in Example 1. The mixed powder was compressed and molded into uncoated tablets in the same manner as in Example 1.

The uncoated tablets obtained include 126.6 mg of the comminuted powder obtained in Example 7, 3.0 mg of corn starch and 0.4 mg of magnesium stearate per tablet (130.0 mg).

Example 8

Corn starch (58.1 g), magnesium stearate (2.8 g) and 9.1 g (1.0% by weight based on the total weight) of powdery stearic acid (m.p. 56° to 72° C.) as an oily or fatty substance having a lower melting point were added to 840 g of the comminuted powder containing Compound A obtained in Example 1, and 910 g of a mixed powder was prepared according to the same procedure as in Example 1. The powdery stearic acid was prepared by pulverizing stearic acid with a mortar and sieving with a round sieve No. 100.

Uncoated tablets were produced in the same manner as in Example 1 using the mixed powder thus obtained. The tablets include, per tablet (130.0 mg), 120.0 mg of the comminuted powder prepared in Example 1, 8.3 mg of corn starch, 0.4 mg of magnesium stearate and 1.3 mg of stearic acid.

Example 9

The procedures of Example 8 were repeated except that 9.1 g (1.0% by weight based on the total weight) of carnauba wax (trade name: Polishing Wax-103, Freund Industries Ltd., m.p. 80° to 86° C.) was used as an oily or fatty substance having a lower melting point instead of stearic acid. Thus uncoated tablets were obtained.

Example 10

Except for using 9.1 g (1.0% by weight based on the total weight) of ethylene oxide-propylene oxide copolymer (trade name: PEP-101, Freund Industrial Co., Ltd., m.p. 50° to 54° C.) comminuted with a mortar and passed through a round sieve No. 100 as an oily or fatty substance having a lower melting point instead of stearic acid, the procedure of Example 8 was repeated to provide uncoated tablets.

Example 11

An uncoated tablet was obtained in the same procedures as in Example 8 except that 9.1 g (1.0% by weight based on the total weight) of polyoxyethylene [160]-polyoxypropylene [30] (trade name: Pullronic F68, Asahi Denka Ltd., Japan, m.p. 46° to 56° C.) comminuted with a mortar and sieved with a round sieve No. 100 was used instead of stearic acid as an oily or fatty substance with a lower melting point.

Example 12

Example 1 was followed with the use of 840 g of the comminuted powder containing Compound A prepared in accordance with Example 1, 63.7 g of corn starch, 2.8 g of magnesium stearate and 3.5 g (approximately 0.38% by weight based on the total weight) of polyethylene glycol 4,000 (m.p. 53° to 57° C.) milled with the Atomizer used in Example 1 as an oily or fatty substance having a lower melting point, to prepare 910 g of a mixed powder. The resulting mixed powder (910 g) was tabletted in the same manner as Example 1 to provide uncoated tablets.

Each tablet (weight: 130.0 mg) thus obtained includes 120.0 mg of the comminuted powder obtained in Example 1, 9.1 mg of corn starch, 0.4 mg of magnesium stearate and 0.5 mg of polyethylene glycol 4,000.

Example 13

The procedures of Example 1 were repeated using 840 g of the comminuted powder containing Compound A obtained in accordance with Example 1, 63.7 g of corn starch, 2.8 g of magnesium stearate and 3.5 g (about 0.38% by weight based on the total weight) of polyethylene glycol 20,000 (m.p. 56° to 64° C.) milled with the Atomizer used in Example 1, to prepare a mixed powder (910 g). Then the mixed powder (910 g) was compressed and molded into uncoated tablets in the same manner as in Example 1.

The formulation of each tablet (weight: 130.0 mg) is 120.0 mg of the comminuted powder obtained in Example 1, 9.1 mg of corn starch, 0.4 mg of magnesium stearate and 0.5 mg of polyethylene glycol 20,000.

Example 14

A comminuted powder was obtained in the same procedure as in Example 1, except that the fluidized-bed granulator used in Example 1 was charged with 800.0 g of lactose and 160.0 g of corn starch, and that 510.4 g of an aqueous solution of 6% by weight of hydroxypropylcellulose containing 1.6 g of Compound B and 20.8 g of polyethylene glycol 6,000 comminuted with the Atomizer was sprayed for fluidized-bed granulation.

In the same manner as in Example 1, 910 g of a mixed powder was prepared from 886.2 g of the comminuted powder, 21.0 g of corn starch and 2.8 g of magnesium stearate. The mixed powder was compression-molded in the same manner as Example 1 to provide uncoated tablets.

The tablets thus obtained contain, per tablet (130.0 mg), 126.6 mg of the comminuted powder (comprising 0.2 mg of Compound B, 100.0 mg of lactose, 20.0 mg of corn starch, 2.6 mg of polyethylene glycol 6,000 (2.0% by weight) and 3.8 mg of hydroxypropylcellulose), 3.0 mg of corn starch and 0.4 mg of magnesium stearate.

The abrasion resistance of the tablets obtained in Examples and Comparative Examples, and the amount of the drug in powder developed or produced by wearing or abrasion of the tablets of Example 6 and Comparative Example 1 were determined as follows.

(1) Determination of the abrasion resistance

A white bottle of inner volume of 80 ml was charged with 50 g of the uncoated tablets and sealed. Then the bottle was installed vertically in a shaker (trade name: Reciproshaker, Taiyo Kagaku Co., Ltd., Japan) and shaken for 30 minutes at a shaking rate of 220 times per minute and with an amplitude of 40 mm.

After completion of shaking, the uncoated tablets were taken out of the bottle with attention and an extent (degree) of attached or affixed powder on the surface of the tablet by wearing or abrasion was evaluated upon the following criteria. Further, after taking out the tablets, the extent of cloudiness (hazing) of the inside bottom of the white bottle due to the powder developed by wearing or abrasion was determined with a spectrophotometer in absorptiometry (reflectance at a wavelength of 500 nm). The values of absorbances were corrected by an absorbance of the white bottle by itself which was preliminary determined.

As a result of a preliminary examination, it was observed a relationship between the criteria of the cloudiness by visual evaluation and the results of absorptiometry as follows:

| Criteria of cloudiness | | Absorptiometry (Reflectance at 500 nm) |
|---|---|---|
| +: | powder was produced in a large amount | 0.25 or more |
| +/−: | powder was produced in a small amount | 0.15 to 0.25 |
| −: | powder was produced scarcely | 0.15 or less |

(2) Assay of the amount of the drug attached inside of the bottle

Compound A was dissolved in acetonitrile, the solution was diluted to a predetermined concentration, and a calibration curve was obtained by determining the absorbency of the solution with a spectrophotometer at 208 nm.

For the tablets of Example 6 and the tablets of Comparative Example 1, the powder attached to the bottle and remained after the abrasion resistance test mentioned above (1) was dissolved in acetonitrile, and the solution was filtered. The absorbance of the filtrate was determined in the same manner as above and the content of the drug in the powder was calculated using the calibration curve. The determined value of the content of the drug was corrected by the absorbance of the additives other than the drug preliminary determined.

The results of the abrasion resistance and the content of the drug in the powder of the uncoated tablets obtained in Examples and Comparative Examples are shown in Table 1.

TABLE 1

| | Oily or fatty substance | | Degree of cloudiness | Absorptiometry (Reflectance) | Amount of drug (μg per tablet) |
|---|---|---|---|---|---|
| | Species | Amount (% by weight) | | | |
| Ex. 1 | PEG 6,000 | 0.1 | + | 0.28 | — |
| Ex. 2 | PEG 6,000 | 0.2 | +/− | 0.16 | — |
| Ex. 3 | PEG 6,000 | 0.4 | − | 0.08 | — |
| Ex. 4 | PEG 6,000 | 0.6 | − | 0.08 | — |
| Ex. 5 | PEG 6,000 | 1.0 | − | 0.07 | — |
| Ex. 6 | PEG 6,000 | 3.0 | − | 0.06 | 0.068 |
| Comp. Ex. 1 | — | — | + | 0.44 | 0.309 |
| Comp. Ex. 2 | — | — | + | 0.43 | — |
| Ex. 7 | PEG 6,000 | approx. 0.4 | − | 0.08 | — |
| Comp. Ex. 3 | — | — | + | 0.51 | — |
| Ex. 8 | Stearic acid | 1.0 | − | 0.07 | — |
| Ex. 9 | Carnauba wax | 1.0 | − | 0.07 | — |

TABLE 1-continued

|  | Oily or fatty substance | | Degree of cloudiness | Absorptiometry (Reflectance) | Amount of drug (μg per tablet) |
| --- | --- | --- | --- | --- | --- |
|  | Species | Amount (% by weight) | | | |
| Ex. 10 | PEP-101 | 1.0 | — | 0.07 | — |
| Ex. 11 | Pullronic | 1.0 | — | 0.05 | — |
| Ex. 12 | PEG 4,000 | approx. 0.4 | — | 0.10 | — |
| Ex. 13 | PEG 20,00 | approx. 0.4 | — | 0.09 | — |
| Ex. 14 | PEG 6,000 | 2.0 | — | 0.08 | — |

Comparison of Examples 1 to 14 with Comparative Examples 1 to 3 in Table 1 clearly indicates that, regardless of species of the drug, the occurrence of powder was significantly suppressed and remarkable improvements in the abrasion resistance by a small amount of the oily or fatty substance having a lower melting point were observed. Further, as apparent from the results of the Example 14, even when the comminuted powder prepared by wet granulation using the oily or fatty substance having a lower melting point was used, the abrasion resistance of the tablet was also specifically improved as other Examples.

Regarding the amount of the drug attached to inside of the bottle by the abrasion resistance test, the amount of the drug of the tablets obtained in Example 6 was smaller than that of the tablets obtained in Comparative Example 1 by a factor of five.

Test Example

A tablet case (TK-50) of a compounding machine (automatic tablet packaging machine, ATC system, manufactured by Sanyo, Co., Ltd., Japan) was charged with the uncoated tablets of Example 3 and the uncoated tablets of Comparative Example 1 respectively, and the tablets were continuously discharged from the machine one by one at a rate of 150 tablets per minute. The abrasion extent (degree) of the surface of the tablets was evaluated in the following manner.

Namely, a white bottle was disposed in the tablet discharging port of the tablet case, the uncoated tablets were discharged and powder developed by wearing or abrasion were recovered with the discharged tablets. Only the uncoated tablets were taken out from the bottle, and the content of Compound A in the remained powder was determined. The amount of the drug was determined during the time course and evaluated as an accumulated drug amount (μg per tablet). The results are shown in Table 2.

TABLE 2

| Number of discharged tablet | Accumulated amount of drug due to abrasion (μg/tablet) | | |
| --- | --- | --- | --- |
|  | 2,000 | 4,000 | 6,000 |
| Example 3 | 0.02 | 0.23 | 0.45 |
| Comparative Example 1 | 0.15 | 0.58 | 1.25 |

As clearly shown in Table 2, the abrasion or wearing amount of the uncoated tablet of Example 3 was, in spite of an extremely small amount of the oily or fatty substance having a lower melting point, significantly reduced and the abrasion resistance was improved two and a half times as much as the tablet of the Comparative Example 1.

What is claimed is:

1. An uncoated tablet having an improved abrasion resistance, which comprises an active ingredient, an excipient and an oily or fatty substance having a melting point of 20° to 90° C., wherein the content of said oily or fatty substance is 0.1% by weight or more and less than 0.5% by weight based on the total weight of the uncoated tablet.

2. A method of improving an abrasion resistance of an uncoated tablet, which comprises incorporating an oily or fatty substance having a melting point of 20° to 90° C., wherein the content of said oily or fatty substance is 0.1% by weight or more and less than 0.5% by weight based on the total weight of the uncoated tablet, into an active ingredient.

3. The method of improving an abrasion resistance of an uncoated tablet according to claim 2, wherein a compression-moldable composition comprising, based on the total weight of the tablet, an effective amount of the active ingredient and 0.1 to 0.45% by weight of a hydrophilic or water-soluble oily or fatty substance having a lower melting point and having an oxyalkylene unit is compressed and molded.

4. The method of improving an abrasion resistance of an uncoated tablet according to claim 3, wherein said compression-moldable composition is compressed and molded at a compression-molding pressure of 100 to 5,000 kg/cm$^2$.

5. The uncoated tablet according to claim 1, wherein said oily or fatty substance is at least one member selected from the group consisting of a hydrocarbon, a higher fatty acid or a salt thereof, a higher alcohol, a wax, a hardened oil, a fatty acid ester, a higher alcohol ether of a polyhydric alcohol and a homo- or copolymer of an alkylene oxide.

6. The uncoated tablet according to claim 1, wherein said oily or fatty substance is a hydrophilic or water-soluble oily or fatty substance.

7. The uncoated tablet according to claim 1, wherein said oily or fatty substance is a homo- or copolymer of an alkylene oxide.

8. The uncoated tablet according to claim 7, wherein said alkylene oxide is ethylene oxide.

9. The uncoated tablet according to claim 7, wherein said homo- or copolymer of an alkylene oxide is a polyethylene glycol.

10. A method of producing an uncoated tablet having an improved abrasion resistance, which comprises incorporating an oily or fatty substance having a melting point of 20° to 90° C., wherein the content of said oily or fatty substance is 0.1% by weight or more and less than 0.5% by weight based on the total weight of the uncoated tablet, into a compression-moldable composition.

11. The uncoated tablet according to claim 1, which comprises an effective amount of the active ingredient, 25 to 99.5% by weight of the excipient and 0.1 to 0.45% by weight of the oily or fatty substance based on the total weight of the tablet.

12. The uncoated tablet according to claim 11, wherein said oily or fatty substance is a hydrophilic or water-soluble oily or fatty substance having a melting point of 40° to 75° C. and having an oxyalkylene unit.

13. The uncoated tablet according to claim 12, wherein said water-soluble substance is a homo- or copolymer of ethylene oxide.

14. The uncoated tablet according to claim 11, which further comprises 0.5 to 30% by weight of a binder based on the total weight of the tablet.

15. The uncoated tablet according to claim 1, wherein when 50 g of said tablet in a bottle of inner volume of 80 ml is shaken for 30 minutes at a shaking rate of 220 times per minutes and with an amplitude of 40 mm, and a reflectance at a wavelength of 500 nm is determined as the degree of cloudiness of the bottom of the bottle, said tablet has said reflectance of 0.01 to 0.3.

16. The uncoated tablet according to claim 1, which is obtainable by compression-molding a compression-moldable composition comprising (i) a granulated powder containing (a) the active ingredient, (b) the excipient and (c) a binder, and (ii) 0.1% by weight or more and less than 0.5% by weight of said oily or fatty substance based on the total weight of the uncoated tablet.

17. The uncoated tablet according to claim 1, which is obtainable by compression-molding a compression-moldable composition comprising a granulated powder containing (a) the active ingredient, (b) the excipient, (c) a binder and (d) 0.1% by weight or more and less than 0.5% by weight of said oily or fatty substance based on the total weight of the uncoated tablet.

18. The method of producing an uncoated tablet according to claim 10, which further comprises compression-molding a compression-moldable composition comprising a granulated powder containing an active ingredient and an excipient, and the oily or fatty substance having a lower melting point.

19. The method of producing an uncoated tablet according to claim 18, wherein said oily or fatty substance is in powdery or granular form.

20. The method of producing an uncoated tablet according to claim 18, wherein the mean particle size of the oily or fatty substance is 1,000 μm or less.

21. The method of producing an uncoated tablet according to claim 18, which comprises compression-molding the compression-moldable composition comprising the granulated powder containing an effective amount of the active ingredient, 25 to 99.5% by weight of the excipient and 0.5 to 30% by weight of a binder based on the total weight of the tablet, and 0.1% by weight or more and less than 0.5% by weight of the powdery or granular oily or fatty substance based on the total weight of the tablet.

22. The method of producing an uncoated tablet according to claim 21, wherein said oily or fatty substance is a powdery or granular hydrophilic or water-soluble oily or fatty substance comprising a homo- or copolymer of an alkylene oxide.

23. The method of producing an uncoated tablet according to claim 18, wherein said granulated powder is a powder obtainable by a wet-granulation.

24. The method of producing an uncoated tablet according to claim 10, which further comprises compression-molding the compression-moldable composition comprising a granulated powder, wherein said granulated powder comprising an active ingredient, an excipient and said oily or fatty substance.

25. The method of producing an uncoated tablet according to claim 24, wherein a compression-moldable composition comprising the granulated powder composed of an effective amount of the active ingredient, 25 to 99.5% by weight of the excipient, 0.5 to 30% by weight of a binder and 0.1% by weight or more and less than 0.5% by weight of the oily or fatty substance based on the total weight of the tablet is compressed and molded into a tablet.

26. The method of producing an uncoated tablet according to claim 24, wherein said granulated powder is a powder obtainable by a wet-granulation.

* * * * *